US00PP24551P3

(12) United States Plant Patent
Cain

(10) Patent No.: US PP24,551 P3
(45) Date of Patent: Jun. 17, 2014

(54) GRAPEVINE 'IFG ELEVEN'

(50) Latin Name: *Vitis vinifera*
Varietal Denomination: IFG Eleven

(75) Inventor: David Cain, Bakersfield, CA (US)

(73) Assignee: International Fruit Genetics, LLC, Bakersfield, CA (US)

( * ) Notice: Subject to any disclaimer, the term of this patent is extended or adjusted under 35 U.S.C. 154(b) by 184 days.

(21) Appl. No.: 13/507,265

(22) Filed: Jun. 18, 2012

(65) Prior Publication Data

US 2013/0340132 P1 Dec. 19, 2013

(51) Int. Cl.
*A01H 5/00* (2006.01)

(52) U.S. Cl.
USPC ..... Plt./207

(58) Field of Classification Search
USPC ..... Plt./207
See application file for complete search history.

*Primary Examiner* — Wendy C Haas

(57) ABSTRACT

This invention is a new and distinctive grapevine 'IFG Eleven' 'IFG Eleven' produces naturally large, elongated, crisp white seedless berries that require little or no exogenous application of gibberellic acid to obtain commercially acceptable berry size and ripen in mid to late season

1 Drawing Sheet

Latin name of the genus and species claimed: *Vitis vinifera*. Variety denomination: 'IFG Eleven'.

BACKGROUND OF THE INVENTION

The new and distinct grapevine described and claimed herein originated from a hand pollinated cross of the IFG 02013-090-033, an unnamed seedless selection from the IFG breeding program and the IFG 01034-069-026 another unnamed seedless selection from the IFG breeding program hybridized in May 2005. The abortive seed traces were subsequently embryo cultured and the resulting plant was planted in the field in April 2006. The present variety of grapevine was selected as a single plant in September 2007 and was first asexually propagated by hardwood cuttings in December 2007. The resulting propagules were planted during April 2008 near Delano, Kern County, Calif. and were found to reproduce true-to-type through at least two generations of asexual reproduction.

BRIEF SUMMARY OF THE INVENTION

The new grapevine 'IFG Eleven' is characterized by producing naturally large, narrow elliptic, seedless berries having very small residual seed traces. Berries are firm, crisp in texture and ripen in mid to late season. Fruits normally ripen in early September near Delano, Calif.

To the inventor's knowledge, the known variety which the new grapevine variety is most similar to is the Thompson Seedless variety. 'IFG Eleven' can be distinguished from the Thompson Seedless variety by ripening almost one month later. The flesh of the 'IFG Eleven' is crisper than the flesh of the Thompson Seedless variety. 'IFG Eleven' does not require applications of gibberellin to thin clusters or size berries to obtain commercially acceptable berry size as is required for the Thompson Seedless variety. The 'IFG Eleven' has lower acidity than the Thompson Seedless variety. The 'IFG Eleven' is much more productive than the Thompson Seedless variety and can be spur pruned while Thompson Seedless requires cane pruning to attain commercially acceptable yields.

BRIEF DESCRIPTION OF THE FIGURE

The accompanying photographic illustration in FIG. 1 illustrates in full color 'IFG Eleven'. The colors are as nearly true as is reasonably possible in a color representation of this type.

DETAILED BOTANICAL DESCRIPTION OF THE INVENTION

Throughout this specification, color names beginning with a small letter signify that the name of that color, as used in common speech, is aptly descriptive. Color names beginning with a capital letter designate values based upon R.H.S. Colour Chart, published by The Royal Horticultural Society, London, England.

Throughout this specification subjective description values conform to those set forth by the International Plant Genetic Resources Institute publication 'Descriptors for Grape' (*Vitis* spp.) (1983) which was developed in collaboration with the Office International de la Vigne et du Vin (OIV) and the International Union for the Protection of New Varieties of Plants (UPOV).

The descriptive matter which follows pertains to 'IFG Eleven' plants grown in the vicinity of Delano, Kern County, Calif. during 2010, and is believed to apply to plants of the variety grown under similar conditions of soil and climate elsewhere:

VINE

General:

*Size*.—Medium.
*Vigor*.—Medium to Weak.
*Density of foliage*.—Medium to Weak.
*Productivity*.—Very productive.
*Root stock*.—Own root.
*Training method*.—Typically spur pruned leaving 2 bud spurs.

Trunk:
*Trunk diameter of 4-year-old vines at 30 cm above the soil line.*—5.5 cm.
*Shape.*—Medium.
*Straps.*—Short — Split.
*Surface texture.*—Medium rough.
*Inner bark color.*—Yellow-Brown; 164A, 165A, B.

SHOOTS

Young shoot:
*Form of tip.*—Fully opened.
*Distribution of anthocyanin coloration of tip.*—Absent.
*Intensity of anthocyanin coloration of tip.*—Absent.
*Density of prostrate hairs of tip.*—Sparse.
*Density of erect hairs of tip.*—Absent.
*Color.*—Yellow-Green; 144A, 146A, B, C.
Woody shoots (mature canes):
*Shape.*—Medium.
*Internode length.*—Short; About 8.5 cm.
*Width at node.*—About 0.9 cm.
*Cross section.*—Circular.
*Surface.*—Striate.
*Main color.*—Yellowish brown; 174B, 177A, B, C.
*Density of erect hairs of nodes.*—None.
*Density of erect hairs on internodes.*—None.
*Growth of axillary shoots.*—Medium; Approximately 26.2 cm.
Flowering shoot:
*Vigor during flowering.*—Strong.
*Attitude during flowering on shoots not tied.*—Semi-erect.
*Color.*—Dorsal side of internodes — Green with Red stripes.
*Color.*—Ventral side of internodes — Green.
*Color.*—Dorsal side of nodes — Green.
*Color.*—Ventral side of nodes — Green.
*Density of prostrate hairs of nodes.*—Very sparse.
*Density of erect hairs of nodes.*—None.
*Density of prostrate hairs on internode.*—Very sparse.
*Density of erect hairs on internode.*—None.
*Anthocyanin coloration of buds.*—Absent.
Tendrils:
*Distribution on the shoot (at full flowering).*—Discontinuous.
*Length of tendril.*—Medium; About 22.4 cm.
*Thickness.*—Medium.
*Color.*—Yellow-Green; N144A, 152C, 151A.
*Form.*—Mostly Trifurcated and Quadfurcated.
*Number of consecutive tendrils.*—2.

LEAVES

Young leaves:
*Color of upper surface of first four distal unfolded leaves.*—Green.
*Average intensity of anthocyanin coloration of six distal leaves prior to flowering.*—Absent or very weak.
*Density of prostrate hairs between veins (lower surface).*—Absent — Very sparse.
*Density of prostrate hairs on veins (lower surface).*—Very sparse.
*Density of erect hairs between veins (lower surface).*—Absent.
*Density of erect hairs on veins (lower surface).*—Very sparse.

Mature leaves:
*Average length.*—About 13.4 cm.
*Average width.*—About 17.5 cm.
*Mature leaf size.*—Large.
*Shape of blade.*—Wedge-shaped.
*Number of lobes.*—5.
*Anthocyanin coloration of main veins on upper side of blade.*—Absent.
*Mature leaf profile.*—Undulate.
*Blistering surface of blade upper surface.*—Medium.
*Leaf blade tip.*—In the plane of the leaf.
*Undulation of margin.*—Slight.
*Thickness.*—Medium.
*Undulation of blade between main and lateral veins.*—Overall.
*Shape of teeth.*—Mixture of both sides straight and both sides convex.
*Length of teeth.*—Medium.
*Ratio length/width of teeth.*—Small.
*Shape of upper lateral sinuses.*—Lobes slightly overlapping — strongly overlapping.
*Depth of upper lateral sinuses.*—Deep.
*General shape petiole sinus.*—Half open.
*Shape of base of upper leaf sinuses.*—U-shaped.
*Tooth at petiole sinus.*—Absent.
*Density of prostrate hairs between veins on lower surface of blade.*—Very sparse.
*Density if erect hairs between veins on lower surface of blade.*—Absent.
*Density of prostrate hairs on main veins on lower surface of blade.*—Sparse.
*Density of erect hairs on main veins on lower surface of blade.*—Sparse.
*Density of prostrate hairs on main veins on upper surface of blade.*—Sparse.
*Density of erect hairs on main veins on upper surface of blade.*—None.
*Autumn coloration of leaves.*—Grey-Yellow; 161A, B, 163A, B, 162A.
Upper surface:
*Color.*—Green; 137A, B.
*Anthocyanin coloration of main veins.*—Absent.
*Surface appearance.*—Semi-glossy — Dull.
*Blistering surface of blade.*—Weak — Medium.
Lower surface:
*Color.*—Green; 146B.
*Anthocyanin coloration of main veins (lower surface).*—Absent.
*Glossiness.*—Weak.
*Surface texture.*—Rugose.
*Surface appearance.*—Dull.
Petiole:
*Length.*—About 10.5 cm.
*Length of petiole compared to middle vein.*—Slightly shorter.
*Density of prostrate hairs on petiole.*—Sparse.
*Density of erect hairs on petiole.*—None.
Buds:
*Bud fruitfulness.*—Basal: Mostly fruitful.
*Position of first fruitful shoot on previous season cane.*—$1^{st}$ to $2^{nd}$ node.
*Time of bud burst.*—Medium; Mar. 10, 2010.

FLOWERS

General:

*Flower sex*.—Hermaphrodite.

*Length of first inflorescence*.—Medium; About 21.3 cm long by 12.3 cm wide.

*Position of first flowering and fruiting node*.—$3^{rd}$-$4^{th}$ node (current season growth).

*Number of inflorescence per flowering shoot*.—1.1 to 2.

*Time of bloom*.—Medium — Late as compared with similar varieties in the growing area of Delano, Calif.

*Date of full bloom*.—May 18, 2010.

FRUIT

General:

*Ripening period*.—Late; Approximately Sep. 16, 2010.

*Use*.—Fresh market.

*Keeping quality*.—Excellent.

*Resistance to*.—Insects: Average typical of *Vitis vinifera* species. Diseases: Average typical of *Vitis vinifera* species.

*Refractometer test*.—Solid-sugar: About 18.8 Brix.

*Brix/acid*.—About 72.3.

*Titratable acidity*.—About 0.26.

*Juice pH*.—About 4.0.

Cluster:

*Mature cluster length* (*peduncle excluded*).—About 35.8 cm.

*Mature cluster width*.—About 14.8 cm.

*Mature cluster weight*.—About 1384 g.

*Bunch density*.—Medium.

*Number of berries*.—About 236.

*Form*.—Conical.

Peduncle:

*Lignification of peduncle*.—Weak.

*Length of peduncle*.—Medium Approximately 5.0 cm.

Berry:

*Uniformity of size*.—Slightly Variable.

*Single berry weight*.—About 8.9 g natural; to about 9.7 g when treated with gibberellic acid.

*Shape*.—Narrow elliptic.

*Seeds*.—Absent.

*Cross section*.—Circular.

*Berry dimensions*.—Longitudinal axis: About 31.1 mm. Horizontal axis: About 21.6 mm.

*Berry firmness*.—Medium.

*Particular flavor*.—Neutral.

*Bloom* (*cuticular wax*).—Medium.

*Berry separation from pedicel*.—Medium.

*Skin color* (*without bloom*).—Yellow-green; N144D, 145A, 151A.

Skin:

*Thickness*.—Medium.

*Texture*.—Medium.

*Reticulation*.—Absent.

*Tenacity*.—Tenacious to flesh.

What is claimed:

1. A new and distinct variety of grapevine as herein illustrated and described.

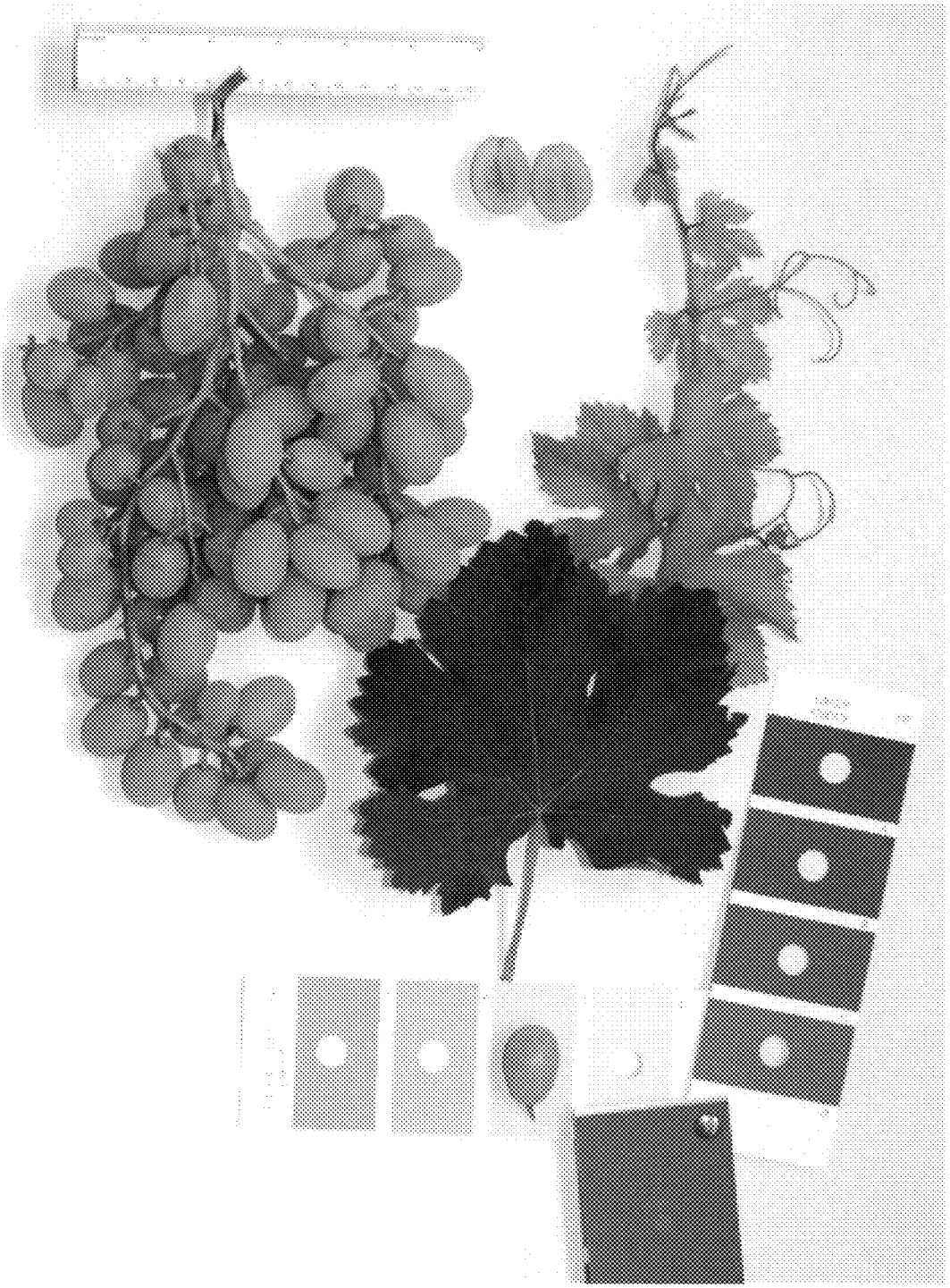

* * * * *